United States Patent
Rungta et al.

(10) Patent No.: US 10,358,401 B2
(45) Date of Patent: Jul. 23, 2019

(54) PROCESS FOR RECOVERING PARA-XYLENE USING A METAL ORGANIC FRAMEWORK ADSORBENT IN A SIMULATED MOVING-BED PROCESS

(71) Applicants: EXXONMOBIL CHEMICAL PATENTS INC., Baytown, TX (US); GEORGIA TECH RESEARCH CORPORATION, Atlanta, GA (US)

(72) Inventors: Meha Rungta, Houston, TX (US); Jeevan S. Abichandani, Houston, TX (US); Dana L. Pilliod, League City, TX (US); Robert G. Tinger, Friendswood, TX (US); Anthony Go, Houston, TX (US); Ke Zhang, Medford, MA (US); Sankar Nair, Atlanta, GA (US); Jason Gee, Houston, TX (US); David Sholl, Marietta, GA (US)

(73) Assignees: EXXONMOBIL CHEMICAL PATENTS INC., Baytown, TX (US); GEORGIA TECH RESEARCH CORPORATION, Atlanta, GA (US)

( * ) Notice: Subject to any disclaimer, the term of this patent is extended or adjusted under 35 U.S.C. 154(b) by 0 days.

(21) Appl. No.: 15/747,951

(22) PCT Filed: Jul. 29, 2016

(86) PCT No.: PCT/US2016/044815
§ 371 (c)(1),
(2) Date: Jan. 26, 2018

(87) PCT Pub. No.: WO2017/048378
PCT Pub. Date: Mar. 23, 2017

(65) Prior Publication Data
US 2018/0215684 A1    Aug. 2, 2018

Related U.S. Application Data

(60) Provisional application No. 62/219,943, filed on Sep. 17, 2015.

(51) Int. Cl.
*C07C 7/12* (2006.01)
*B01D 15/18* (2006.01)
(Continued)

(52) U.S. Cl.
CPC ............ *C07C 7/12* (2013.01); *B01D 3/143* (2013.01); *B01D 15/185* (2013.01);
(Continued)

(58) Field of Classification Search
None
See application file for complete search history.

(56) References Cited

U.S. PATENT DOCUMENTS

| | | | |
|---|---|---|---|
| 3,761,533 A | 9/1973 | Otani et al. | |
| 2010/0282080 A1 | 11/2010 | Omary et al. | |

(Continued)

FOREIGN PATENT DOCUMENTS

| | | | | |
|---|---|---|---|---|
| WO | 2013011210 A1 | 1/2013 | | |
| WO | WO-2013011201 A1 * | 1/2013 | ............ | H04W 8/245 |
| WO | 2014033481 A2 | 3/2014 | | |

OTHER PUBLICATIONS

Machine translation WO 2013/011210. Jan. 24, 2013. (Year: 2013).*

(Continued)

*Primary Examiner* — Philip Y Louie
*Assistant Examiner* — Alyssa L Cepluch
(74) *Attorney, Agent, or Firm* — Roberts Mlotkowski Safran Cole & Calderon P.C.

(57) ABSTRACT

Para-xylene is separated from a mixture of C8 aromatics using a simulated moving bed (SMB) adsorption process, wherein a MOF is used as an adsorbent and an alkane or (Continued)

alkene having 7 or less carbon atoms, such as hexane or heptane is used as desorbent. Because of the difference in boiling points of a hexane or heptane desorbent as compared to conventional desorbents such as toluene or para-diethylbenzene, less energy is required to separate hexane or heptane from C8 aromatics by distillation than the energy required to separate toluene or diethylbenzene from C8 aromatics by distillation.

13 Claims, 1 Drawing Sheet

(51) Int. Cl.
*B01D 3/14* (2006.01)
*C07C 5/27* (2006.01)
*C07C 7/00* (2006.01)
*C07C 7/04* (2006.01)

(52) U.S. Cl.
CPC ..... *B01D 15/1821* (2013.01); *B01D 15/1828* (2013.01); *C07C 5/277* (2013.01); *C07C 5/2732* (2013.01); *C07C 7/005* (2013.01); *C07C 7/04* (2013.01); *Y02P 20/57* (2015.11)

(56) References Cited

U.S. PATENT DOCUMENTS

2012/0004491 A1* 1/2012 Kulprathipanja ......... C07C 7/12
585/828

2013/0233698 A1* 9/2013 Corradi ................. B01D 3/143
203/41
2016/0250618 A1 9/2016 Long et al.

OTHER PUBLICATIONS

International Search Report issued in the corresponding application PCT/US2016/044815 dated Oct. 18, 2016.
Moreira et al. "Effect of ethylbenzene in p-xylene selectivity of the porous titanium amino terephthalate MIL-125(Ti)_NH2", Microporous and Mesoporous Materials 158 (2012) 229-234.
Moreira et al.—"Hybrid process for o- and p-xylene production in aromatics plants", Chemical Engineering and Technology (2014), vol. 37, No. 9, pp. 1483-1492.
Peralta et al.—"Adsorption and separation of xylene isomers: CPO-27-Ni vs HKUST-1 vs NaY", Journal of Physical Chemistry C (Oct. 18, 2012), vol. 116, No. 41, pp. 21844-21855.
Moreira et al.—"Influence of the eluent in the MIL-53(Al) selectivity for xylene isomers separation", Industrial and Engineering Chemistry Research (Jun. 15, 2011), vol. 50, No. 12, pp. 7688-7695.
Peralta et al.—"The separation of xylene isomers by ZIF-8: A demonstration of the extraordinary flexibility of the ZIF-8 framework", Microporous and Mesoporous Materials (Jun. 2013), vol. 173, pp. 1-5.
Gu et al.—"Adsorption and separation of xylene isomers and ethylbenzene on two Zn-terephthalate metal-organic frameworks", Journal of Physical Chemistry C (Jan. 14, 2010), vol. 114, No. 1, pp. 311-316.
Lahoz-Martin et al.—"Selective separation of BTEX mixtures using metal-organic frameworks", Journal of Physical Chemistry C (Jun. 19, 2014), vol. 118, No. 24, pp. 13126-13136.

* cited by examiner

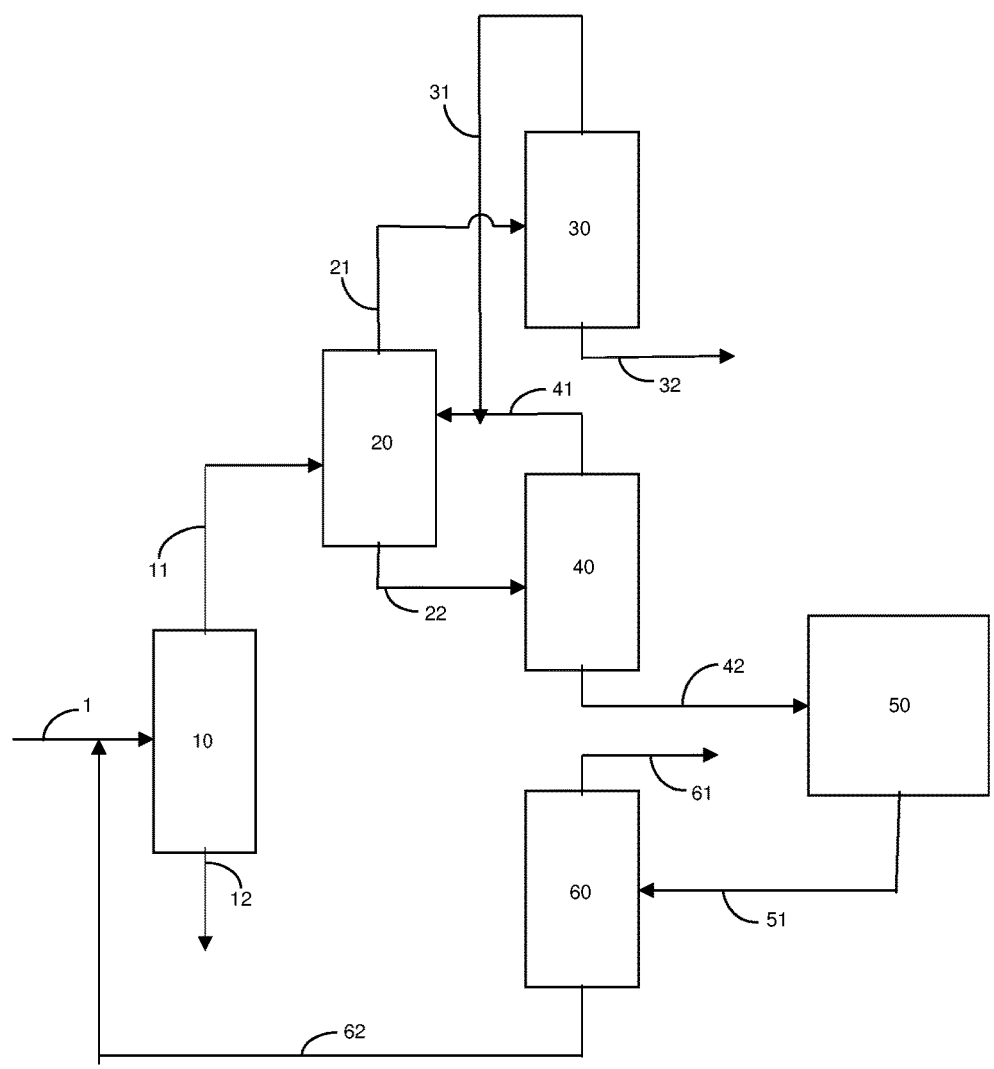

PROCESS FOR RECOVERING PARA-XYLENE USING A METAL ORGANIC FRAMEWORK ADSORBENT IN A SIMULATED MOVING-BED PROCESS

CROSS-REFERENCE TO RELATED APPLICATIONS

The present application is a U.S. National Phase of PCT/US2016/044815 filed on Jul. 29, 2016 claiming priority to provisional U.S. Patent application Ser. No. 62/219,943 filed Sep. 17, 2015. The disclosure of the PCT Application is hereby incorporated by reference into the present Application.

FIELD OF THE INVENTION

This invention relates to a process for separating para-xylene from a mixture of C8 aromatics in a simulated moving-bed process using a para-xylene selective Metal Organic Framework (MOF) as an adsorbent.

BACKGROUND OF THE INVENTION

Ethylbenzene (EB), para-xylene (PX), ortho-xylene (OX) and meta-xylene (MX) are present together in many C8 aromatic product streams from chemical plants and oil refineries. While all these species have important uses, market demand for para-xylene, used extensively as starting material for making synthetic fibers, is greater than for the other C8 aromatic isomers.

Given the higher demand for PX as compared with its other isomers, there is significant commercial interest in maximizing PX production from any given source of C8 aromatic materials. However, there are two major technical challenges in achieving this goal of maximizing PX yield. First, the four C8 aromatic compounds, particularly the three xylene isomers, are usually present in concentrations dictated by the thermodynamics of production of the C8 aromatic stream in a particular plant or refinery. As a result, the PX production is typically limited to the amount originally present in the C8 aromatic stream, which is, again in the typical case, approximately 24 mol % at thermal equilibrium, unless additional processing steps are used to increase the amount of PX and/or to improve the PX recovery efficiency. Secondly, the C8 aromatics are difficult to separate due to their similar chemical structures and physical properties and identical molecular weights.

A variety of methods are known to increase the concentration of PX in a C8 aromatics stream. These methods normally involve a loop system comprising a separation step, in which at least part of the PX is recovered (and removed from the system in a PX-enriched stream), leaving a PX-depleted stream, the latter being sent to a xylene isomerization step, in which the PX content of the PX-depleted stream is returned back towards thermal equilibrium concentration and recycled to the separation step.

The separation step may be accomplished using fractional crystallization techniques, which are based on the difference on the freezing points of the C8 aromatic isomers, or adsorption separation techniques, which are based on the selectivity of adsorbent for one isomer over another. Amongst the well-known adsorption separation techniques are the UOP Parex™ Process and the Axens Eluxyl™ Process.

A prior art system including the separation step and isomerization steps referred to above generally will include the use of numerous fractionation towers, e.g., a reformate splitter, a benzene recovery tower, a toluene recovery tower, a xylene rerun tower, an isomerization unit heptanizer, and one or more towers associated with the adsorption separation unit, e.g., Eluxyl™ adsorptive separation unit(s). A system comprising a Eluxyl™ adsorptive separation unit using PDEB (para-diethylbenzene) as a desorbent ("heavy" Eluxyl™ adsorptive separation unit) will have an extract tower, raffinate tower(s) and finishing tower(s) while a system comprising a Parex™ adsorptive separation unit using toluene as a desorbent ("light" Parex™ adsorptive separation unit) only needs the extract and raffinate towers, since the extract tower separates out both the toluene in the desorbent stream as well as trace toluene in the xylene feed. In a plant using both types of units the light extract tower can serve as the finishing tower for the heavy unit.

The isomerization step typically is accomplished by contact with a molecular sieve catalyst, such as ZSM-5, under appropriate conditions to convert a para-xylene-depleted mixture of C8 aromatic hydrocarbons to thermodynamic equilibrium amounts. Historically xylene isomerization has been accomplished in the vapor phase, however recently liquid isomerization units have found increasing use in para-xylene separation systems.

It is known that liquid phase isomerization technology can reduce energy usage in an aromatics plant by reducing the amount of feed to vapor phase isomerization. Vapor phase isomerization requires more energy due to the phase change in the isomerization process. In addition, vapor phase isomerization requires more fractionation energy in the isomerization system's heptanizer and xylene rerun tower.

In a simulated moving-bed apparatus, such as a Eluxyl™ unit, examples of adsorbents include charcoal, ion-exchange resins, silica gel, activated carbon, zeolitic material, and the like. An adsorbent, which is particularly useful for separating para-xylene from other C8 aromatics, is a faujasite-type molecular sieve material, such as zeolite X or zeolite Y, optionally, substituted or treated with an enhancing agent, such as a Group I or II element, such as potassium or barium. Examples of adsorbents for separating para-xylene from other C8 aromatics are described in U.S. Pat. No. 3,761,533.

It has recently been discovered that certain Metal Organic Frameworks (MOFs) are para-xylene selective adsorbents, whereas other MOFs are ortho-xylene selective adsorbents. The para-xylene selective MOFs have a greater affinity for para-xylene than other C8 aromatics. In U.S. Pat. No. 8,704,031, two MOFs are said have excellent selectivity to para-xylene, and another MOF is said have good selectivity for ortho-xylene. The para-xylene selective MOFs are Al-MIL-53 and Zn-MOF-5. The ortho-xylene selective MOF is Cr-MIL-101. These MOF adsorbents may be used in a simulated moving bed unit. U.S. Pat. No. 8,704,031 also describes desorbents for such MOFs. Such desobents include aromatics, such as para-diethylbenzene, toluene and 1,4-diisopropylbenzene.

The extract stream from a simulated moving bed unit for separating PX from MX, OX and EB includes para-xylene and desorbent. The raffinate extract stream from such a simulated moving bed unit includes MX, OX, EB and desorbent. Desorbent is separated from C8 aromatics by distillation.

Para-diethylbenzene has a boiling point at atmospheric pressure of 183.9° C. Toluene has a boiling point at atmospheric pressure of 110.6° C. C8 aromatics have boiling points at atmospheric pressure within the range of about 136° C. to about 145° C. Accordingly, in order to separate desorbent from C8 aromatics by distillation the extract or raffinate must be heated above the boiling point of C8 aromatics, when diethylbenzene is used as the desorbent, and the extract or raffinate must be heated above the boiling point of toluene, when toluene is used as the desorbent. These distillations require the use of considerable amounts of energy.

Accordingly, it would be desirable to provide a simulated moving-bed adsorptive separation process for separating para-xylene from a mixture of para-xylene and at least other C8 aromatic, wherein less energy is used to separate desorbent from C8 aromatics.

SUMMARY OF THE INVENTION

There is provided herein a simulated moving-bed adsorptive separation process for separating para-xylene from a mixture of para-xylene and at least other C8 aromatic, wherein a MOF is used as an adsorbent and a non-aromatic, such as hexane or heptane is used as desorbent. Hexane has a boiling point at atmospheric pressure of 68.5° C. Heptane has a boiling point at atmospheric pressure of 98.4° C. Thus, less energy is required to separate hexane or heptane from C8 aromatics by distillation than the energy required to separate toluene or diethylbenzene from C8 aromatics by distillation.

Replacing zeolite based materials with MOFs in a simulated moving bed process allows the use of low boiling non-aromatic desorbents which require lower energy for separation. Additional energy savings may be realized by using low level waste heat for separating xylenes from non-aromatic components, and/or relaxing the raffinate purity specifications by allowing some non-aromatics to slip with the raffinate stream and be cracked in vapor phase isomerization.

In the inventive process, a feed stream comprising para-xylene and at least one other C8 aromatic, such as at least one of meta-xylene, ortho-xylene and ethylbenzene, is introduced into a simulated moving-bed adsorptive apparatus having multiple beds containing adsorbent material in step (a). The adsorbent material comprises a para-xylene selective Metal Organic Framework (MOF). Examples of the para-xylene selective MOF used as an adsorbent include MIL-125-NH$_2$, MIL-140b, ZIF-8, MOF-48 and mixtures thereof.

A desorbent stream is then introduced into the simulated moving-bed adsorptive apparatus in step (b). The desorbent stream of step (b) comprises at least 50 wt %, for example, at least 90 wt %, for example, at least 95 wt %, of one or a mixture of linear or branched alkanes or alkenes having 7 or less carbon atoms, and is preferably selceted from the group consisting of n-hexane and n-heptane. An extract stream comprising desorbent and para-xylene is withdrawn from the simulated moving-bed adsorptive apparatus in step (c), and in step (d), at least one raffinate stream, comprising desorbent and at least one of meta-xylene, ortho-xylene and ethylbenzene, is withdrawn from the simulated moving-bed adsorptive apparatus. In step (e), a flow of circulating fluid is maintained throughout the simulated moving-bed adsorptive apparatus, and in step (f), the flow of streams into and out of the simulated moving-bed adsorptive apparatus is switched to a bed downstream in terms of the direction of the circulating fluid at a set time interval.

The process may further comprise passing the raffinate stream from step (d) to a distillation zone, which is maintained under conditions sufficient to obtain an overhead stream comprising desorbent and a bottoms stream comprising meta-xylene, ortho-xylene and ethylbenzene. At least a portion of the overhead stream comprising desorbent is recycled and used as desorbent in step (b). At least a portion of the bottoms stream comprising meta-xylene, ortho-xylene and ethylbenzene is passed to an isomerization zone, which is maintained under conditions sufficient to produce a product stream comprising para-xylene, which is then recycled and used as a portion of the feed stream in step (a). In one embodiment, the bottoms stream from the distillation zone may also comprise at least a portion of the desorbent, which may be cracked in the isomerization zone operating under vapor phase conditions.

BRIEF DESCRIPTION OF THE DRAWINGS

FIGURE shows a process flow diagram for separating para-xylene from a mixture of C8 aromatics.

DETAILED DESCRIPTION

A process to separate para-xylene from a mixture of C8 aromatics using a simulated moving bed (SMB) adsorption process is provided, wherein a MOF is used as an adsorbent and an alkane or alkene having 7 or less carbon atoms, such as hexane or heptane is used as desorbent. Because of the difference in boiling points of a hexane or heptane desorbent as compared to conventional desorbents such as toluene or para-diethylbenzene, less energy is required to separate hexane or heptane from C8 aromatics by distillation than the energy required to separate toluene or diethylbenzene from C8 aromatics by distillation.

FIGURE shows, in a diagramatic fashion, examples of features of a process for separating para-xyxlene from a mixture of C8 aromatics. In FIG. 1, introduction of feed into a distillation zone 10 is represented by line 1. The feed, which is introduced through line 1 may include a C8 aromatic mixture produced by at least one refinery or petrochemical process. Examples of refinery or petrochemical processes for producing the feed of step (a) include a reforming process, an isomerization process, a transalkylation process, a selective toluene disproportionation process, a selective benzene or toluene methylation process, and a selective process for converting methanol to para-xylene.

In distillation zone 10, the components of the feed are separated into an overhead stream including C8 aromatics and bottoms stream including C9+hydrocarbons (i.e., hydrocarbons having 9 or more carbon atoms, such as trimethylbenzene). The removal of the overhead stream from distillation zone 10 is represented by line 11. The removal of the bottoms stream from distillation zone 10 is represented by line 12.

C8 aromatics in line 11 are introduced into separation zone 20. The separation zone 20 includes a simulated moving bed unit equipped with a device, such as a rotary valve, for introducing streams into and out of the adsorbtion beds of the unit. The adsorbent in the beds of the separation zone 20 comprises at least one MOF. An extract stream, which comprises para-xylene and a desorbent, is removed from the separation zone 20, via line 21. A raffinate stream, which comprises at least one of meta-xylene, ortho-xylene, ethylbenzene and a desorbent, is removed from the separation zone 20, via line 22. A desorbent stream is introduced into the separation zone 20, via line 41.

The desorbent introduced into the separation zone 20 comprises at least 50 wt % of one or a mixture of linear or branched alkanes or alkenes having 7 or less carbon atoms. Alkanes or alkenes having 7 or less carbon atoms are also referred to here as C7– alkanes or alkenes. The desorbent may be sourced from a naphtha cut, that is free of sulfur and nitrogen contaminants, and having an initial boiling point of 50° C. or more and final boiling point of 110° C. or less. Examples of desorbent streams include streams comprising at least 90 wt %, for example, at least 95 wt %, for example, at least 99 wt % of at least one linear alkane selected from the group consisting of n-hexane and n-heptane.

The extract stream in line 21 is introduced into distillation zone 30. An overhead stream, which comprises desorbent, is withdrawn from distillation zone 30 via line 31. Desorbent in line 31 is combined with desorbent in line 41 and introduced into separation zone 20. Para-xylene is withdrawn as a bottoms stream from distillation zone 30 via line 32.

The raffinate stream in line 22 is introduced into distillation zone 40. An overhead stream, which comprises desorbent, is withdrawn from distillation zone 40 via line 41. Desorbent in line 41 is combined with desorbent in line 31 and introduced into separation zone 20. Meta-xylene, ortho-xylene and ethylbenzene is withdrawn as a bottoms stream from distillation zone 40 via line 42.

Meta-xylene, ortho-xylene and ethylbenzene in line 42 is introduced into isomerization zone 50. Para-xylene is generated in isomerization zone 50 by an isomerization reaction. The product stream is withdrawn from isomerization zone 50 via line 51. The procuct stream comprises para-xylene meta-xylene, ortho-xylene and ethylbenzene.

The product stream in line 51 is introduced into distillation zone 60. An overhead stream, which comprises hydrocarbons having 7 or less carbon atoms (i.e. C7– hydrocarbons) is withdrawn from distillation zone 60 via line 61. A bottoms stream, which comprises para-xylene meta-xylene, ortho-xylene and ethylbenzene, is withdrawn from distillation zone 60 via line 62. This stream is combined with feed in line 1 and introduced into distillation zone 10.

MOF Structures

One known family of porous crystalline materials are metal organic frameworks or MOFs. These frameworks have metal ions or clusters of metal ions and organic molecules called linkers. The pores of metal organic frameworks may be used for the storage of gases, such as hydrogen and carbon dioxide. Metal organic frameworks may also be used for gas purification, gas separation, catalysis and sensors.

Metal organic framework materials are described in U.S. Pat. Nos. 5,648,508; 7,662,746; and U.S. Patent Publication No. 2009/0305040.

Various MOF materials have been developed at the Lavoisier Institute in Versailles with various phases, called "MIL" (for "Material Institute Lavoisier"). The designation "MIL"of these structures is followed by an arbitrary number n given by inventors for identifying the different phases. Various MIL materials are described in U.S. Patent Publication No. 2015/0150981.

In addition to an MIL material, another type of MOF material is a ZIF material. ZIF stands for zeolitic imidazolate framework. These ZIF materials may be described as having a tetrahedral framework comprising a general structure, $M^1$-IM-$M^2$, wherein $M^1$ and $M^2$ comprises the same or different metal, and wherein IM is imidazolate or a substituted imidazolate linking moiety.

ZIF's include such structures iso-structural to known zeolites, for example, those identified in U.S. Patent Publication No. 2007/0202038 and U.S. Patent Publication No. 2010/037336, including ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAG, CAN, CAS, CDO, CFI, CGF, CGS, CHA, CHI, CLO, CON, CRB, CZP, DAC, DDR, DFO, DFT, DIA, DOH, DON, EAB, EDI, EMT, EON, EPI, ERI, ESV, ETR, EUO, EZT, FAR, FAU, FER, FRA, FRL, GIS, GIU, GME, GON, GOO, HEU, IFR, IHW, ISV, ITE, ITH, ITW, IWR, IWV, IWW, JBW, KFI, LAU, LCS, LEV, LIO, LIT, LOS, LOV, LTA, LTL, LTN, MAR, MAZ, MEI, MEL, MEP, MER, MFI, MFS, MON, MOR, MOZ, MSE, MSO, MTF, MTN, MTT, MTW, MWW, NAB, NAT, NES, NON, NPO, NSI, OBW, OFF, OSI, OSO, OWE, PAR, PAU, PHI, PON, POZ, RHO, RON, RRO, RSN, RTE, RTH, RUT, RWR, RWY, SAO, SAS, SAT, SAV, SBE, SBS, SBT, SFE, SFF, SFG, SFH, SFN, SFO, SGT, SIV, SOD, SOS, SSY, STF, STI, STT, SZR, TER, THO, TON, TSC, TUN, UEI, UFI, UOZ, USI, UTL, VET, VFI, VNI, VSV, WEI, WEN, YUG, ZNI, and ZON. Such structures include a tetrahedral framework type selected from the group consisting of CRB, DFT, CAG, SOD, MER, RHO, ANA, LTA, DIA, ZNI, GME, LCS, FRL, GIS, POZ, MOZ. All of these framework types have been realized in the syntheses of ZIFs.

Suitable MOFs for use in the present separation process may be determined by testing MOFs on their ability to sorb C8 aromatics and the ability of C7– alkanes and alkenes to desorb the C8 aromatics. A suitable test method is decribed an Example described hereinafter.

Examples of suitable MOFs include MIL-125-$NH_2$, MIL-140b, ZIF-8 and MOF-48. MIL-125-$NH_2$ is described in US20120085235 A1. MIL-140b is described in Angew. Chem. Int. Ed. 2012, 51, 9267. ZIF-8 is described in United States Patent Publication No. US 2007/0202038A1 to Yaghi et al. MOF-48 is described in Inorg. Chem. 2011, 50, 7388.

The C8 Aromatic Feed

At least 50 volume percent of the C8 aromatic mixture may be produced by at least one refinery or petrochemical process. Examples of refinery or petrochemical processes for producing equilibrium xylenes for the C8 aromatic feed of step (a), which mixture comprises from 15 to 30 volume percent of para-xylene, include a reforming process, an isomerization process, a transalkylation process and a mixture of any of these processes. An example of a refinery or petrochemical process for producing enhanced para-xylene, which comprises from 75 to 98 volume percent of para-xylene, which may be used as at least a portion of the C8 aromatic feed of step (a), is a selective toluene disproportionation process, a selective benzene or toluene methylation process, or a selective process for converting methanol to para-xylene.

At least a portion of the mixture of C8 aromatics fed to the simulated moving-bed adsorptive apparatus may be formed by a reforming process. The reforming process may comprise passing a mixture of hydrocarbons comprising naphtha into a reforming unit. In the reforming unit, at least a portion of the naphtha unit is converted into aromatic compounds comprising benzene, toluene, xylenes and ethylbenzene. The effluent from the reforming unit may be distilled to separate xylenes and ethylbenzene from other aromatics. The naphtha feed comprises a mixture of hydrocarbons may comprise C6, C7 and C8 paraffins.

At least a portion of the mixture of C8 aromatics used as a feed to the simulated moving-bed adsorptive apparatus may be formed by a transalkylation process. The transalkylation process may comprise passing a mixture of toluene and trimethylbenzene into a transalkylation unit. At least a portion of the toluene and trimethylbenzene in the transalkylation unit is converted into aromatic compounds comprising xylenes and ethylbenzene.

At least a portion of the mixture of C8 aromatics used as a feed to the simulated moving-bed adsorptive apparatus may be formed by an isomerization process. Xylenes obtained from a raffinate stream may be used as a feed to this isomerization process to bring the xylenes back to their equilibrium concentrations.

A selective process may be used for producing a mixture of C8 aromatics enriched in para-xylene. These para-xylene enriched C8 aromatics may be used as at least a portion of the feed to the simulated moving-bed adsorptive apparatus. Non-limiting examples of these processes include a selective toluene disproportion process (STDP), a selective toluene alkylation process, a selective benzene alkylation process and a selective process for converting methanol to para-xylene. These processes may be conducted in the presence of a shape selective molecular sieve catalyst. The molecular sieve may be a zeolite, for example, a medium pore size zeolite, such as ZSM-5. The molecular sieve may be treated with one or more selectivating agents, such as phosphorus or magnesium compounds, to increase the shape selectivity of the catalyst. Examples of processes for selective toluene disproportionation are described in U.S. Pat. No. 5,365,004. Examples of processes for selective toluene alkylation with a methanol alkylating agent are described in International Publication No. WO 2013/330093. Examples of processes for the selective conversion of methanol to para-xylene are described in U.S. Patent No. 4,088,706. The selective toluene alkylation process may involve replacing at least a portion of toluene reactant with benzene and forming toluene in situ prior to converting such toluene to C8 aromatics.

Isomerization of the Distilled Raffinate

A large variety of xylene isomerization processes are known and any of these processes can be used with the present adsorption process. For example, it may be desirable to employ a xylene isomerization process that is effective to convert ethylbenzene in the C8 aromatic feedstream to other compounds, such as by isomerization to xylenes or by cracking to benzene and a C2 component. Examples of suitable xylene isomerization processes are disclosed in U.S. Pat. Nos. 4,899,011; 5,516,946; 5,689,027; 6,028,238; 6,924,405; and 7,683,233.

In one embodiment, each xylene isomerization step employed in the present process is conducted in the presence of at least two catalyst components, the first of which has the primary function of selectively deethylating the ethylbenzene in the feedstream to benzene, while the second catalyst component selectively isomerizes xylenes in the feed. The first catalyst component can, and preferably will, effect some isomerization of the xylenes in the feed.

Each of the first and second catalyst components comprises an intermediate pore size molecular sieve which is characterized by a Constraint Index within the approximate range of 1 to 12 (e.g., less than about 7 Angstroms pore size, such as from about 5 to less than about 7 Angstroms). The method by which Constraint Index is determined is described fully in U.S. Patent No. 4,016,218, incorporated herein by reference for details of the method. Examples of intermediate pore size molecular sieves useful in the present process include ZSM-5 (U.S. Pat. Nos. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780).

The molecular sieve of each of the first and second catalyst components is preferably associated with a hydrogenation-dehydrogenation component. Examples of such components include the oxide, hydroxide, sulfide, or free metal (i.e., zero valent) forms of Group 8 to 10 metals (i.e., Pt, Pd, Ir, Rh, Os, Ru, Ni, Co and Fe), Group 6 metals (i.e, Cr, Mo, W), Group 14 metals (i.e., Sn and Pb), Group 15 metals (i.e., Sb and Bi), and Group 7 metals (i.e., Mn, Tc and Re). As used herein, the new numbering scheme for the Periodic Table Groups are as disclosed in Chemical and Engineering News, 63(5), 27 (1985). Combinations of catalytic forms of such noble or non-noble metal, such as combinations of Pt with Sn, may be used. The metal is preferably in a reduced valence state, e.g., when this component is in the form of an oxide or hydroxide. The reduced valence state of the metal may be attained, in situ, during the course of a reaction, when a reducing agent, such as hydrogen, is included in the feed to the reaction. In one preferred embodiment, the hydrogenation-dehydrogenation component is a noble metal (i.e., Pt, Pd, Ir, Rh, Os and Ru) and most preferably is platinum. In a further preferred embodiment, the hydrogenation-dehydrogenation component is an early transition metal, such as molybdenum, tungsten, rhenium and/or manganese, typically rhenium.

Each of the components of the catalyst system will normally exhibit mutually exclusive xylene diffusional properties. These properties can be identified by noting the time (in minutes) required to sorb 30% of the equilibrium capacity of ortho-xylene at 120° C. and at an ortho-xylene partial pressure of 600±107 Pa (4.5±0.8 mm of mercury), a test described in U.S. Pat. Nos. 4,117,026; 4,159,282; and Re. 31,782. The equilibrium capacity of ortho-xylene is defined herein as greater than 1 gram of xylene(s) per 100 grams of molecular sieve. In the catalyst system, the first catalyst component effective for ethylbenzene conversion typically has an ortho-xylene sorption time (in minutes) in excess of about 50 minutes, such as greater than about 1200 minutes, but normally less than 10,000 minutes, while on the other hand, the second, isomerization component typically has an ortho-xylene sorption time of less than about 50 minutes, such as less than about 10 minutes.

The desired xylene diffusion properties of the first catalyst component can be achieved in a number of ways. For ortho-xylene diffusion times at or near the minimum value of 50 minutes, the selection of a large crystal form of the molecular sieve used in the catalyst, that is having an average crystal size in excess of 1 micron, may be sufficient. However, to achieve higher diffusivity values, it may be desirable to selectivate the first catalyst component by deposition on the surface of the catalyst particles of a layer of coke and/or an oxide, such as silica, which is inert under the process conditions experienced in use. Where the catalyst particles are selectivated, both large crystal size and medium crystal size (having a crystal size of 0.2-0.5 micron) molecular sieves can be used in the first catalyst component. Where the first catalyst component is to be selectivated with silica, this is conveniently achieved by subjecting the catalyst to one or more treatments with an organosilicon compound in a liquid carrier, each treatment being followed by calcination of the treated material in an oxygen containing atmosphere, e.g., air. Such a multiple selectivation procedure is described in U.S. Pat. No. 5,476,823.

The second catalyst component, which is effective to isomerize xylenes, preferably has an ortho-xylene sorption time of less than about 50 minutes and preferably less than about 10 minutes. This is typically achieved by using a small crystal size molecular sieve, having an average crystal size of 0.02-0.05 micron, in this component. The molecular sieve of the second component of the catalyst system will typically have an alpha value less than about less than 50 and preferably from about 5 to about 25.

In general, the xylene isomerization step is carried out in a fixed bed reactor containing the catalyst system described above. In one embodiment, the first and second components of the catalyst system are in sequential beds in a single reactor. That is, the component of the catalyst system used in the process of the invention which is effective for ethylbenzene conversion forms a first bed, while the other component of the catalyst system, which is effective for xylene isomerization, forms a second bed downstream of the first bed. The feed is typically cascaded from the first to the second bed without intervening separation of light gases. As an alternative, the first and second beds could be disposed in separate reactors which, if desired, could be operated at different process conditions.

The conditions used in the xylene isomerization step are not narrowly defined, but generally will include a temperature of from about 200° C. to about 540° C., a pressure of from about 0 to about 1,000 psig (100 to 7000 kPa), a weight hourly space velocity (WHSV) of between about 0.1 and about 200 hr$^{-1}$, and a hydrogen, $H_2$, to hydrocarbon, HC, molar ratio of between about 0.2 and about 10. Preferably, the conditions include a temperature of from about 340° C. to about 450° C., a pressure of from about 50 and about 400 psig (445 and 2860 kPa), a WHSV of between about 3 and about 50 hr$^{-1}$ and a $H_2$ to HC molar ratio of between about 1 and about 5.

EXAMPLE

A mixture of xylenes containing PX, MX, OX and EB was passed over the adsorbent (zeolite or MOF) pre-saturated with the desorbent at various temperatures. Once the adsorbtion was complete, evident from pX breakthrough and effluent composition reaching the feed composition, the bed was subject to a desorbent to remove the adsorbed species. For the zeolite case, toluene was used as the desorbent and for the MOFs case n-heptane was used as the desorbent. The process was repeated over 3 adsorption-desorption cycles.

Table 1 shows the pX selective features of several MOFs as compared to the zeolites used in current practice. Table 2 shows the boiling point difference between the xylenes and the desorbents. The larger difference will lead to easier separation, resulting in energy savings.

TABLE 1

Summary of Xylene Separation Performances

| Material | Breakthrough Temperature [° C.] | Capacity [mmol/g] | PX/EB | PX/MX | PX/OX |
|---|---|---|---|---|---|
| MIL-125 (Ti)—NH$_2$ Heptane Desorbent | 50 | 1.3 | 1.3 | 1.5 | 1.6 |
| MIL-140b (Zr) Heptane Desorbent | 50 | 1.2 | 2.1 | 1.6 | 1.8 |
|  | 100 | 0.9 | 1.9 | 1.4 | 1.7 |
|  | 150 | 0.7 | 1.7 | 1.3 | 1.5 |
| ZIF-8 (Zn) Heptane Desorbent | 100 | 1.4 | 1.2 | 1.8 | 2.2 |
|  | 150 | 1.2 | 1.3 | 2.0 | 2.3 |
| MOF-48 (V) Heptane Desorbent | 50 | 1.1 | 1.5 | 1.7 | 1.7 |
| Current state-of-art zeolite BaX Toluene Desorbent | 50 | 2.2 | 1.2 | 1.2 | 1.1 |
|  | 90 | 2.0 | 1.3 | 1.4 | 1.1 |
|  | 120 | 1.9 | 1.4 | 1.4 | 1.2 |
|  | 150 | 1.6 | 1.6 | 1.5 | 1.3 |
|  | 180 | 1.4 | 1.9 | 1.6 | 1.4 |

TABLE 2

Boiling points of xylenes and desorbents.

| Compound | Boiling Point [° C.] | Difference in Boiling Point* [° C.] |
|---|---|---|
| o-xylene | 144.4 | — |
| m-xylene | 139.1 | — |
| p-xylene | 138.4 | — |
| Ethylbenzene | 136.2 | — |
| p-diethylbenzene | 183.9 | 45 |
| Toluene | 110.6 | 28 |
| n-heptane | 98.4 | 40 |
| n-hexane | 68.5 | 70 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for separating para-xylene from a mixture of para-xylene and at least one other C8 aromatic by simulated moving-bed adsorptive separation, said process comprising the steps of:
    (a) introducing a feed stream, which comprises para-xylene and at least one other C8 aromatic, into a simulated moving-bed adsorptive apparatus, wherein said simulated moving-bed adsorptive apparatus comprises multiple beds containing adsorbent material;
    (b) introducing a desorbent stream, which comprises desorbent, into the simulated moving-bed adsorptive apparatus;
    (c) withdrawing an extract stream, which comprises desorbent and para-xylene, from the simulated moving-bed adsorptive apparatus;
    (d) withdrawing at least one raffinate stream, which comprises desorbent and at least one C8 aromatic, which is different from the para-xylene in the extract stream of step (c), from the simulated moving-bed adsorptive apparatus;
    (e) maintaining a flow of circulating fluid throughout the simulated moving-bed adsorptive apparatus; and
    (f) switching the flow of streams into and out of the simulated moving-bed adsorptive apparatus to a bed downstream in terms of the direction of the circulating fluid at a set time interval,
        wherein the desorbent stream of step (b) comprises at least 50 wt % of one or a mixture of linear or branched alkanes or alkenes having 7 or less carbon atoms, and
        wherein the adsorbent material of step (a) comprises a para-xylene selective Metal Organic Framework (MOF) selected from the group consisting of MIL-140b, ZIF-8 and MOF-48.

2. The process of claim 1, wherein the desorbent stream of step (b) comprises at least 90 wt % of one or a mixture of linear or branched alkanes or alkenes having 7 or less carbon atoms.

3. The process of claim 1, wherein the desorbent stream of step (b) comprises at least 50 wt % of a naphtha cut, that is free of sulfur and nitrogen contaminants, and having an initial boiling point of 50° C. or more and final boiling point of 110° C. or less.

4. The process of claim 1, wherein the desorbent stream of step (b) comprises at least 90 wt % of at least one linear alkane selceted from the group consisting of n-hexane and n-heptane.

5. The process of claim 1, wherein the desorbent stream of step (b) comprises at least 99 wt % of n-hexane.

6. The process of claim 1, wherein the desorbent stream of step (b) comprises at least 99 wt % of n-heptane.

7. The process of claim 1, wherein the mixture of at least two aromatics comprises para-xylene, meta-xylene, ortho-xylene and ethylbenzene, and wherein the raffinate stream of step (d) comprises meta-xylene, ortho-xylene and ethylbenzene.

8. The process of claim 7 further comprising the steps of:
(g) passing the raffinate stream from step (d) to a distillation zone;
(h) maintaining the distillation zone of step (g) under conditions sufficient to obtain an overhead stream comprising desorbent and a bottoms stream comprising meta-xylene, ortho-xylene and ethylbenzene;
(i) using at least a portion of the overhead stream of step (h) as desorbent in step (b);
(j) passing at least a portion of the bottoms stream from step (h) to an isomerization zone;
(k) maintaining the isomerization zone of step (j) under conditions sufficient to produce a product stream comprising para-xylene; and
(l) using at least a portion of the para-xylene in the product stream from step (k) as a portion of the feed stream in step (a).

9. The process of claim 7, wherein the bottoms stream from step (h) comprises at least a portion of the C7– alkane or alkene introduced into the distillation zone of step (h);
wherein the isomerization zone of step (k) is maintained under vapor phase conditions; and
wherein C7– alkane or alkene is cracked in the isomerization zone of step (k).

10. A process for separating para-xylene from a mixture of para-xylene, meta-xylene, ortho-xylene and ethylbenzene by simulated moving-bed adsorptive separation in a simulated moving-bed adsorption apparatus comprising multiple beds containing adsorbent material, including a step of introducing the mixture into the apparatus, introducing a desorbent stream into the apparatus, withdrawing an extract stream from the apparatus and withdrawing at least one raffinate stream from the apparatus, the improvement comprising using a para-xylene selective Metal Organic Framework (MOF) selected from the group consisting of MIL-140b, ZIF-8 and MOF-48 as the adsorbent material and at least 50 wt % of one or a mixture of linear or branched alkanes or alkenes having 7 or less carbon atoms for the desorbent stream.

11. The process of claim 10, wherein the desorbent stream of step (b) comprises at least 90 wt % of at least one linear alkane selceted from the group consisting of n-hexane and n-heptane.

12. The process of claim 10, wherein the desorbent stream of step (b) comprises at least 99 wt % of n-hexane.

13. The process of claim 10, wherein the desorbent stream of step (b) comprises at least 99 wt % of n-heptane.

* * * * *